United States Patent [19]

Curtis et al.

[11] Patent Number: 4,997,642
[45] Date of Patent: Mar. 5, 1991

[54] STABLE OIL-IN-WATER EMULSIONS

[75] Inventors: Ralston Curtis, Mountain View; Howard R. Brownell, Palo Alto; Steven C. Papanu, Los Altos, all of Calif.

[73] Assignee: Sandoz Ltd., Basel, Switzerland

[21] Appl. No.: 362,892

[22] Filed: Jun. 5, 1989

Related U.S. Application Data

[63] Continuation of Ser. No. 89,183, Aug. 25, 1987, abandoned, which is a continuation-in-part of Ser. No. 732,526, May 9, 1985, abandoned, which is a continuation-in-part of Ser. No. 447,548, Dec. 7, 1982, abandoned, which is a continuation-in-part of Ser. No. 334,187, Dec. 24, 1981, abandoned.

[51] Int. Cl.$^5$ .......................................... A61K 31/74
[52] U.S. Cl. .......................................... 424/78; 424/81; 424/678; 424/681; 424/718; 424/722; 424/723; 71/4; 71/31; 71/54; 71/64.08; 71/64.09; 71/64.1; 71/125; 514/521; 514/540

[58] Field of Search ................. 424/78, 81, 153, 144, 424/154; 71/4, 31, 64.08, 64.09, 64.1, 54, 125; 514/521, 540

[56] References Cited

U.S. PATENT DOCUMENTS

| | | | |
|---|---|---|---|
| 3,060,084 | 10/1962 | Littler | 167/42 |
| 4,174,960 | 11/1979 | Hendriksen | 71/121 |
| 4,243,819 | 1/1981 | Henrick et al. | 562/433 |
| 4,252,796 | 2/1981 | Yu et al. | 424/179 |
| 4,260,633 | 4/1981 | Anderson et al. | 424/304 |
| 4,283,415 | 8/1981 | Fuyama et al. | 424/304 |
| 4,324,781 | 4/1982 | Okamoto et al. | 424/78 |
| 4,460,406 | 7/1984 | Valange | 71/100 |

*Primary Examiner*—Hoa V. Le
*Attorney, Agent, or Firm*—Allen E. Norris

[57] ABSTRACT

Oil-in-water emulsions containing polyvinyl alcohol, surfactant and a salt with improved freeze-thaw and elevated temperature storage stability.

12 Claims, No Drawings

STABLE OIL-IN-WATER EMULSIONS

This is a continuation of application Ser. No. 089,183 filed Aug. 25, 1987 abandoned which in turn is a continuation-in-part of Ser. No. 732,526, filed May 9, 1985 abandoned, which is a continuation-in-part of Ser. No. 447,548, filed Dec. 7, 1982, now abandoned, which is a continuation-in-part of Ser. No. 334,187, filed Dec. 24, 1981, now abandoned.

This invention relates to novel oil-in-water emulsions which are freeze-thaw stable and 50° C. storage stable and which are easily dispersed in water. In one aspect, the invention relates to any water-insoluble oily compound dispersed in water. In another aspect, this invention relates to oil-in-water emulsions containing insecticides such as synthetic pyrethroids, or other pesticidal compounds such as plant growth regulators, herbicides, and fungicides, the preparation thereof, and the use of said emulsions for the control of pests.

U.S. Pat. No. 4,283,415 discloses oil-in-water pesticidal emulsions having emulsified particles from 1 to 200 microns in size, polyvinyl alcohol or gum arabic and a thickener. Particle size is large, and suspension stability is achieved only in a viscous mixture containing a thickener, which thickener is a requirement of the patented composition. In general, oil-in-water pesticidal emulsions containing surfactants and organic thickeners such as carboxymethylcellulose and vegetable gums are well known.

The limitations of the prior art oil-in-water emulsions are their lack of particle size stability during 50° C. storage as well as their general lack of stability during severe freeze-thaw cycles.

The present invention is directed to an inventive solution to the stability problem encountered with oil-in-water emulsions. An initially stable oil-in-water emulsion, after being frozen and thawed, separates into a single oil phase and a single water phase on standing. Constant storage and transportation at temperatures above freezing would be required to maintain the prior art compositions in a useful form. The present invention is a novel, surprising solution to the problem, one which has broad application not limited to any particular oily compound.

The oil-in-water concentrates of this invention are stable, aqueous emulsions having freeze-thaw stability, 50° C. storage stability, and easy dispersibility when diluted with water. In summary, the composition of this invention is a stable oil-in-water emulsion consisting essentially of (a) from 1 to 50% by weight of a water-insoluble oily compound dispersed as particles having an average size of less than one micron;
(b) from 2 to 20% by weight of polyvinyl alcohol having a molecular weight of from 2000 to 125,000 and having from 11 to 28% of its hydroxy groups present as the acetate ester;
(c) from 0.1 to 8% by weight of a surfactant;
(d) from 0.1% by weight to saturation concentration of a salt;
(e) the balance being water;

the emulsion being freeze-thaw stable and 50° C. storage stable.

Oily water-insoluble materials which are to be dispersed in water for general purposes present severe mixing problems. It is a general object of this invention to provide a composition wherein the oily compounds are dispersed in an oil-in-water emulsion concentrate so that they can be handled with convenience and practicality to formulate more dilute dispersions. This problem is particularly aggravated in the pesticide art where the pesticidally active compounds are frequently encountered as thick, water-insoluble oils.

Prior to this invention, pesticidal dispersions have required thickeners to maintain stability. In the compositions of the present invention, a thickener is not needed for stability. The elimination of the thickener not only saves in cost of material and processing steps, but it provides a more pourable formulation.

The conventionally used type of liquid pesticidal formulation, an emulsifiable concentrate (EC), contains as its major ingredient a large amount of organic solvent. Drawbacks of this formulation, due to the organic solvent therein, include phytotoxicity to plants, eye and skin irritation to animals and humans, flammability, and the like. The EC formulation is also very sensitive to extremes in water temperature and water hardness.

For these reasons, aqueous, organic solvent-free formulations such as the oil-in-water emulsions of this invention provide a major advance. In the compositions of this invention where the oily component is a pesticidally active compound, the pesticidal activity is equivalent to or exceeds that of a conventional EC formulation. It is stable even at extremes of environmental temperatures, and it is easy and convenient to use. Furthermore, it is much less irritating to skin and eyes, nonflammable and shows no phytotoxicity.

The emulsions of this invention can be diluted in water without difficulty in temperature extremes and in water having up to 20,000 ppm hardness. To do this is very difficult or impossible with an EC formulation. A further advantage of the emulsion of this invention is the ease of its dispersion when it is diluted with water, for example in a tank sprayer.

Generally speaking, the nature of the active ingredient in the dispersion compositions of this invention is not critical. It is necessary only that the compound be a water-insoluble oily compound having a solubility in water of less than one weight percent and a viscosity of at least one cps at 25° C. (measured by a Brookfield LV using a no. 1 spindle at 60 rpm). It is with thicker oils that the emulsion concentrates of this invention offer the greatest advantage.

The emulsion compositions of this invention are particularly useful when the water-insoluble oil is a pesticide. "Pesticide" includes insecticides, herbicides, plant growth regulators and fungicides. Insecticides include, for example, malathion, fentrothion, dimethoate, fluvalinate, permethrin, cypermethrin, fenvalerate, deltamethrin and fenpropathrin. Herbicides include, for example, trifluralin, alachlor, bensulide, butylate and diclofop-methyl.

A particularly advantageous composition of this invention is obtained when the pesticidally active compound in the composition is fluvalinate, α-cyano-3-phenoxybenzyl 2-(2-chloro-4-trifluoromethylphenylamino)-3-methylbutanoate. This compound can be obtained as a racemic mixture of four diastereomers or the individual diastereomers. Of most particular value are oil-in-water concentrates wherein the oily component is the half-resolved (S,R)-α-cyano-3-phenoxybenzyl (R)-2-(2-chloro-4-trifluoromethylphenylamino)-3methylbutanoate, described in U.S. Pat. Number 4,260,633.

These pesticides are normally present as a thick viscous oil, and after some prolonged storage of the diastereomer mixtures, crystal growth may occur within the dispersed particles. Dispersions of such partially crystallized components are included within the terms "oil-in-water dispersion" and "oil-in-water emulsion" as used herein. Water-insoluble low melting solids which are solid at room temperature but are viscous oils when heated can be dispersed in the aqueous medium in the heated, liquid state to form an emulsion of particles having a size of less than one micron. After cooling, the initially oily liquid particles solidify, yielding a dispersion of solid particles. Such dispersions are also included within the terms "oil-in-water dispersion" and "oil-in-water emulsion" as used herein, and such compounds are included within the term "oily compound" as used herein.

In the oil-in-water emulsions of this invention, the oily compound is dispersed in particles having an average size of less than one micron. Particles of one micron or smaller in size are very important to maintaining stability of the oil-in-water emulsion. Larger particle size causes separation into oil and aqueous phases. Thus, minimum growth in particle size during freeze-thaw cycling and prolonged 50° C. storage is critical. The concentration of the oily component is from one to 50 weight percent and preferably from 20 to 30 weight percent in the emulsion concentrate of this invention.

The composition of this invention contains from 2 to 20 weight percent and preferably from 5.5 to 8.5 weight percent polyvinyl alcohol. Polyvinyl alcohol suitable for use in the composition of this invention has a molecular weight of from 2000 to 125,000 and is about 72 to 89 mole percent hydrolyzed; that is, has from 11 to 28 percent of its hydroxy groups present in the acetate ester form. Such alcohols include GELVATOL 20/90 (Monsanto), which is 88.7 to 85.5 mole percent hydrolyzed, and MOWIOL 40-88 (American Hoechst), which is 88.7 to 86.7 mole percent hydrolyzed, both of which have an average molecular weight of 125,000; GELVATOL 40/10, which is 77 to 72.9 mole percent hydrolyzed and has an average molecular weight of 2000 or over; and GELVATOL 20/30, which is 89 to 87.7 mole percent hydrolyzed, and MOWIOL 5-88, which is 88.7 to 86.7 mole percent hydrolyzed, both of which have an average molecular weight of about 10,000. In contrast, a completely hydrolyzed polyvinyl alcohol, such as ELVANOL (DuPont, less than one percent residual polyvinyl acetate), causes failure of the mixture to emulsify.

The composition of this invention contains from 0.1 to 8 weight percent surfactant. The surfactants suitable for use in the composition of this invention include anionic, cationic, non-ionic and amphoteric surfactants and compatible mixtures thereof. Surfactants suitable for use in the formulation of the present invention are, for example, blended surfactants which are designed by the manufacturer specifically for use in emulsifiable concentrates of synthetic organic pesticides. These surfactants are believed to be blends of common anionic and non-ionic surfactants with the most functionally significant component being alkali or alkaline earth alkaryl sulfonate, such as calcium dodecylbenzene sulfonate. Their use in this invention is a novel application not intended by the manufacturer. Such a surfactant may be chosen from, for example, TOXIMUL D (Stepan Chemical); TRITON AG-180, AG-190 or AG-193 (Rohm & Haas); the ATLOX series (Imperial Chemical Industries); and the SPONTO series (Witco).

Another class of surfactants suitable for use in the formulation of the present invention is sodium naphthalene formaldehyde condensates. Examples of such surfactants are PETRO DISPERSANT 425 (Petro Chemicals Co., Inc.), BLANCOL N (GAF) and TAMOL N (Rohm & Haas).

Non-ionic surfactants suitable for use in the composition of this invention include surfactants such as TRITON CF-21 (Rohm & Haas), a modified ethoxylated non-ionic surfactant. Amphoteric surfactants such as DERIPHAT BAW (Henkel), cocoamidoebetaine and LONZAINE 10S and 12C (Lonza, Inc.), decylbetaine and cocobetaine can be used in the composition of this invention. Examples of suitable cationic surfactants include ETHOMEEN C-15 and T-15 (Industrial Chemical Division of Armac, Inc.), tertiary amine-ethylene oxide condensation products of primary fatty amines, tallow amines and cocoamines.

The preferred surfactants are the anionic on the amphoteric surfactants.

The composition of this invention also contains from 0.1 weight percent to saturation concentrations (at 20° C.), and preferably from 5 to 30 percent by weight of a salt such as calcium chloride, calcium nitrate, magnesium chloride, magnesium nitrate, potassium bromide, potassium iodide, sodium nitrate or mixtures thereof. Polyvinyl alcohol solubility may be reduced at the highest salt concentrations. The optimum salt concentration is from 10 to 20 percent by weight. In view of the well-known properties of inorganic salts to cause flocculation and precipitation of dispersed phases and to otherwise destabilize an emulsion, it is unexpected that stability can be achieved in the presence of substantial quantities of these salts. It is even more surprising, with these specific inorganic salts, that not only is the freeze-thaw stability greatly increased but stability on prolonged storage at 50° C. is also greatly increased. Prior to this invention, particle size growth of oily particles in aqueous emulsions could not be easily retarded during prolonged 50° C. storage.

The balance of the composition of this invention is water.

The emulsions of the present invention can be prepared by dispersing liquid particles of the water-insoluble oil by mechanical means, with or without a surfactant, in an aqueous mixture of polyvinyl alcohol, water and the inorganic salt. Thus, the active ingredient is first premixed until uniform with a surfactant. This mixture is added to the aqueous mixture in a conventional stirrer such as a WARING Blender, a SORVALL OMNI-MIXER or a KRAFT apparatus non-aerating stirrer, usually at a high speed and with heating to a temperature of from 60° to 70° C. In the stirrer, the liquid particles of the active ingredient are dispersed in the aqueous phase. Stirring with heating is continued for about 10 to 20 minutes, that is, until the particle size average is less than one micron and all individual particles are less than 2 and preferably less than one micron in diameter.

The terms "dispersion" and "emulsion" are used interchangeably herein to denote a two-phase liquid system in which small droplets of one liquid (an oil) are immiscible in and are dispersed uniformly throughout a second, continuous liquid phase (water).

The term "freeze-thaw stable", as used herein with reference to oil-in-water emulsions, is defined to mean the respective emulsion has passed the Freeze-Thaw Cycle Test. This test is as follows:

Freeze-Thaw Cycle Test (1) A 5 to 10 ml sample of emulsion is placed in a 10 ml screw-top glass vial and capped.

(2) The vial is placed in a freezing compartment for 16 hours to −15° C. It is then removed and allowed to sit at 24° C. for 8 hours.

(3) Repeat Step 2 twice more (to give a total of 3 cycles).

(4) Examine the emulsion. The sample must show no visual signs of oiling (separation of the oil component) or solidification. The sample should move and flow as freely with minimal hand stirring as it did before the test. Unless all of these requirements are satisfied, the emulsion is not freeze-thaw stable.

The term "50° C. storage stable", as used herein with reference to oil-in-water emulsions, is defined to mean the respective emulsion has passed the 50° C. Storage Test. This test is as follows:

50° C. Storage Test (1) A 50 g sample of the emulsion is stored at 50° C. in a capped glass vial or other sealed container.

(2) The particle size of this sample is checked at the end of an extended period of time, usually 30 days, using one of two procedures:

(a) The sample is shaken, and ten drops of the emulsion are added to a GRANULOMETRE 715 (Compagnie Industrielle des Lasers) which measures the percentage and size of particles present; or (b)
(1) The sample is shaken, and one drop (from a pipette) is added to 5 ml of deionized water and shaken until homogeneous;
(2) Two drops of this dispersed sample are placed on a microscope slide and covered with a cover glass;
(3) Examine slide with a microscope using an oil-immersion lens under 1000x magnification;
(4) Count the number of particles having a diameter greater than 3 microns in an 18 mm$^2$ viewing area. If not more than 10 particles are observed having diameters greater than 5 microns, the test is passed.

The formulations of the present invention containing pesticidally active components are concentrates. Before normal use, these concentrates are diluted with water to a concentration providing from 0.01 to 0.1 weight percent of the active ingredient. Therefore, the ability of the composition to disperse easily in water is critical. For example, α-cyano-3-phenoxybenzyl 2-(2-chloro-4-trifluoro-methylphenylamino)-3-methylbutanoate is a highly active pesticide, particularly against insects, mites and ticks. Among the pests against which the compound is pesticidally effective are insects of the order Lepidoptera, Orthoptera, Heteroptera, Homoptera, Diptera, Coleoptera or Hymenoptera, and mites and ticks of the class Acari, including mites of the family Tetranychides or Tarsonemidae and ticks of the family Argasidae or Ixodidae.

In the use of the formulation of the present invention for combatting pests, the formulation containing pesticide is applied to the pest or its locus in a pesticidally effective amount by spraying or other methods known in the art.

The following examples are provided to illustrate the practice of the present invention. Temperature is given in degrees Celsius. Percentages are given as percent by weight.

EXAMPLE 1

23 Grams of half-resolved fluvalinate, 1.0 g of Deriphat BAW, 22.4 g of deionized water and 5.6 g of Gelvatol 20/30 were mixed for 7 minutes at top speed in a Waring Blender, model 8590 (25 ml to 250 ml capacity). A cooling jacket prevents the temperature from rising above 50° C. 20 Grams of anhydrous calcium chloride dissolved in 28 g of deionized water was then added and mixed at top speed for 5 minutes.

Microscopic examination confirmed that all of the particles were submicron. The emulsion was subjected to the Freeze-Thaw Stability Test and 50° C. Storage Stability Test and found to have passed both.

EXAMPLE 2

11.2 Grams of half-resolved fluvalinate, 0.5 g of Deriphat BAW, 14.2 g of deionized water and 2.8 g of Gelvatol 20/30 were mixed for 7 minutes in a Waring Blender. The temperature did not rise above 50° C. 8.7 Grams of anhydrous calcium chloride dissolved in 12.6 g of deionized water was then added and mixed at top speed for 5 minutes.

The resulting oil phase particles of the oil-in-water flowable emulsion were mostly submicron in diameter with a few one micron particles as determined by microscopic examination. The emulsion also passed the Freeze-Thaw Stability and 50° C. Storage Stability Tests.

EXAMPLE 3

11.2 Grams of technical cypermethrin, 0.4 g of Deriphat BAW, 2.2 g of Gelvatol 20/30 and 13.0 g of deionized water were mixed for 7 minutes in a Waring Blender. 6.0 Grams of anhydrous calcium chloride dissolved in 7.2 g of deionized water was then added and mixed at top speed for 5 minutes.

The particle size was one micron and less, and the emulsion passed the Freeze-Thaw Test. (Cypermethrin is (RS)-α-cyano-3-phenoxybenzyl (1RS)-cis,trans-3-(2,2-dichloro-vinyl)-2,2-dimethylcyclopropanecarboxylate.)

EXAMPLE 4

11.3 Grams of technical grade fenvalerate, 0.5 g of Deriphat BAW, 2.8 g of Gelvatol 20/30 and 14.2 g of deionized water were mixed for 7 minutes in a Waring Blender. 8.7 Grams of anhydrous calcium chloride dissolved in 12.5 g of deionized water was then added and mixed at top speed until all of the particles were one micron or less in size. The emulsion passed the Freeze-Thaw Test. (Fenvalerate is -cyano-3-phenoxybenzyl 2-(4-chlorophenyl)-3-methylbutanoate.)

EXAMPLE 5

The procedure of Example 4 was repeated with the exception that 7.5 g of anhydrous calcium chloride was dissolved in 11.7 g of deionized water and added to the blender. The particle size was submicron, and the emulsion passed the Freeze-Thaw Test.

EXAMPLE 6

11.5 Grams of technical grade permethrin, 0.5 g of Deriphat BAW, 2.8 g of Gelvatol 20/30 and 16.2 of deionized water were mixed at top speed for 7 minutes in a Waring Blender. 7.5 Grams of anhydrous calcium chloride dissolved in 11.5 g of deionized water was added and mixed at top speed until all of the particles were one micron or less in diameter. The emulsion passed the Freeze-Thaw Test. (Permethrin is 3-phenoxybenzyl (1RS)-cis,trans-3-(2,2-dichlorovinyl)-2,2-dimethylcyclopropanecarboxylate.)

EXAMPLE 7

The procedure of Example 6 was repeated with the exception that 8.7 g of anhydrous calcium chloride dissolved in 12.3 g of deionized water was added to the blender. The particles were all submicron in size, and the emulsion passed the Freeze-Thaw Test.

EXAMPLE 8

Using an uncooled Waring Blender, Model 8580, trifluralin technical (23 g) was dispersed into a mixture of Gelvatol 20/30 (5.8 g), water (22.2 g) and Deriphat BAW (1 g) using high speed mixing. The temperature was allowed to rise naturally from mixing friction to 40°-50° to insure melting of the trifluralin. In total, three one-minute cycles of mixing with alternate cooling to 20°-25° reduced the particle size to less than 1 micron. Then, CaCl$_2$ (20 g) and water (28 g) were added and mixed at high speed for two minutes. Physical tests showed excellent freeze-thaw stability and no effects from storage.

Trifluralin is the common name for 2,6-dinitro-N,N-dipropyl-4-trifluoromethylaniline.

EXAMPLE 9

Following the procedure of Example 1, two formulations were prepared, each identical with the other except that Formulation #1 contained calcium chloride while Formulation #2 contained additional water in place of the salt. The initial particle size of each was submicron to 1 micron.

After 28 days at 28° C., Formulation #1 maintained a particle size of submicron to 1 micron, whereas the particle size of Formulation #2 had increased to 2–3 microns.

|  | Weight % | |
| --- | --- | --- |
|  | Formulation #1 | Formulation #2 |
| Half-resolved fluvalinate | 23.0 | 23.0 |
| Deriphat BAW | 1.0 | 1.0 |
| Gelvatol 20/30 (20% soln. in water) | 28.0 | 28.0 |
| deionized water | 28.0 | 48.0 |
| anhydrous calcium chloride | 20.0 | — |

EXAMPLE 10

An emulsion premix (A) was prepared in a 1 qt. Osterizer by shearing a dispersion of half-resolved fluvalinate (88% a.i.; 44.2 g), Mowiol 5-88 (10.7 g), deionized water (43.2 g) and Deriphat BAW (1.9 g) at high speed until all particles are less than 1 micron in size (as measured by Granulometre 715), about 2 min.

One-half of the premix was diluted with a calcium chloride solution and the other with water alone, as follows:

|  | B | C |
| --- | --- | --- |
| premix (A) | 52.0 g | 52.0 g |
| deionized water | 28.0 | 48.0 |
| calcium chloride | 20.0 | — |

Samples (B) and (C) were held at 54° C. and were checked at intervals for particle size (on the Granulometre). The result in Table A show that formulation (B), containing the salt, maintained 100% of its particles less than 1 micron in size whereas over time the particles of formulation C began to increase.

TABLE A

| Time | Particle Size | Formulation B | Formulation C |
| --- | --- | --- | --- |
| initial | <1 micron | 100.0% | 100.0% |
| 7 days | <1 micron | 100.0 | 100.0 |
| 12 days | <1 micron | 100.0 | 88.7 |
|  | 1–1.5 microns | 0 | 11.3 |
| 21 days | <1 micron | 100.0 | 71.7 |
|  | 1.15 microns | 0 | 22.5 |
|  | 1.5–2 microns | 0 | 5.8 |

What is claimed is:

1. A stable oil-in-water emulsion consisting essentially of:
   (a) from 1 to 50% by weight of a water-insoluble oily compound having a solubility in water of less than one weight percent and viscosity of at least one cps at 25° C., dispersed as particles having an average size of less than one micron;
   (b) from 2 to 20% by weight of polyvinyl alcohol having a molecular weight of from 2000 to 125,000 and having from 11 to 28% of its hydroxy groups present as the acetate ester;
   (c) from 0.1 to 8% by weight of an anionic, cationic, non-ionic or amphoteric surfactant;
   (d) from 0.1% by weight up to saturation concentration of a salt selected from the group consisting of calcium chloride, calcium nitrate, magnesium chloride, magnesium nitrate, potassium bromide, potassium iodide, sodium nitrate and mixtures thereof;
   (e) the balance being water; the emulsion being freeze-thaw stable and 50° C. storage stable.

2. The emulsion of claim 1 wherein the water-insoluble oily compound is pesticidally active and concentration of salt is from 5 to 30% by weight.

3. The emulsion of claim 2 wherein the water-insoluble oily compound is an insecticide or a herbicide.

4. The emulsion of claim 3 wherein the water-insoluble oily compound is (S,R)-α-cyano-3-phenoxybenzyl (R)-2-(2chloro-4-trifluoromethylphenylamino)-3-methylbutanoate.

5. The emulsion of claim 4 wherein the concentration of the water-insoluble oily compound is from 20 to 30% by weight.

6. The emulsion of claim 5 wherein the concentration of salt is from 10 to 20% by weight.

7. The emulsion of claim 6 wherein the salt is calcium chloride.

8. A composition comprising the oil-in-water emulsion of claim 1 diluted with sufficient water to provide a concentration of from 0.01 to 0.1 weight percent oily compound.

9. The composition of claim 8 wherein the water-insoluble oily compound is pesticidally active.

10. The composition of claim 9, wherein the water-insoluble oily compound is an insecticide or herbicide.

11. The composition of claim 10 wherein the water-insoluble oily compound is (S,R)α-cyano-3-phenoxybenzyl (R)-2(2-chloro-4-trifluoromethylphenylamino)-3-methylbutanoate.

12. The composition of claim 11 wherein the salt is calcium chloride.

* * * * *